United States Patent
Kim et al.

(10) Patent No.: US 11,661,445 B2
(45) Date of Patent: May 30, 2023

(54) PROMOTER POLYNUCLEOTIDE, SIGNAL POLYPEPTIDE AND USE THEREOF

(71) Applicant: LIVEOME Inc., Suwon-si (KR)

(72) Inventors: Young In Kim, Seongnam-si (KR); Ji Yoon Song, Seongnam-si (KR); Ji Ae Yun, Suwon-si (KR); Seung Kee Cho, Suwon-si (KR); Hyeon Jin Noh, Suwon-si (KR)

(73) Assignee: LIVEOME INC., Gyeonggi-Do (KR)

( * ) Notice: Subject to any disclaimer, the term of this patent is extended or adjusted under 35 U.S.C. 154(b) by 306 days.

(21) Appl. No.: 16/959,058

(22) PCT Filed: Nov. 8, 2018

(86) PCT No.: PCT/KR2018/013520
§ 371 (c)(1),
(2) Date: Jun. 29, 2020

(87) PCT Pub. No.: WO2019/132231
PCT Pub. Date: Jul. 4, 2019

(65) Prior Publication Data
US 2020/0339637 A1    Oct. 29, 2020

(30) Foreign Application Priority Data
Dec. 29, 2017 (KR) .................. 10-2017-0184819

(51) Int. Cl.
*C07K 14/335* (2006.01)
*C12N 15/74* (2006.01)

(52) U.S. Cl.
CPC ............ *C07K 14/335* (2013.01); *C12N 15/74* (2013.01); *C07K 2319/02* (2013.01)

(58) Field of Classification Search
CPC .............. C07K 14/335; C07K 2319/02; C12N 15/74
See application file for complete search history.

(56) References Cited

U.S. PATENT DOCUMENTS 8,748,381 B2    6/2014    Polk et al.
8,759,088 B2    6/2014    Steidler et al.

FOREIGN PATENT DOCUMENTS

JP    2010515445 A    5/2010
WO    2008084115 A2    7/2008
WO    2011039137 A1    4/2011

OTHER PUBLICATIONS

NCBI Gen Bank Accession No. CP016355.1 (Dec. 7, 2017) (Year: 2017).*
Zhang et al. 2010 (Complete Genome Sequence of *Lactobacillus casei* Zhnag, a New Probiotic Strain Isolated from Traditional Homemade Koumiss in Inner Mongolia, China; Journal of Bacteriology; 192(19): 5268-5269). (Year: 2010).*
DATABASE UniProt [Online] May 27, 2015 (May 27, 2015), "RecName: Full=Peptidase C51 domain-containing protein {ECO:0000259| Prosite:PS50911}", XP55831074; retrieved from EBI accession No. UNIPROT: A0A0E2LY68.
Extended European Search Report dated Aug. 20, 2021 for EP Patent Application No. 18897474.5.
Ida Rud et al., "A synthetic promoter library for constitutive gene expression in *Lactobacillus plantarum*" Microbiology (2006) vol. 152, No. part 4, pp. 1011-1019.
JP Office Action dated Jul. 27, 2021 of JP Patent Application No. 2020-535620.
Djordjevic et al., "Cloning of promoter-like sequences from *Lactobacillus paracasei* subsp. paracasei CG11 and their expression in *Escherichia coli, Lactococcus lactis,* and *Lactobacillus reuteri*," Canadian Journal of Microbiology, 1994, vol. 40, pp. 1043-1050, Canadian Science Publishing, Canada.
International Search Report and Written Opinion dated May 15, 2019, issued in International Application No. PCT/KR2018/013520.
NCBI, "*Lactobacillus paracasei* subsp. paracasei strain TMW 1.1434 chromosome, complete genome," GenBank accession No. CP016355.1 (Dec. 7, 2017).
NCBI, "CHAP domain-containing protein [*Lactobacillus paracasei*]," GenBank accession No. WP_019894997.1 (Jun. 8, 2016).
NCBI, "CHAP domain-containing protein, partial [*Lactobacillus paracasei*]," GenBank accession No. WP_019900131.1 (Jun. 8, 2016).

* cited by examiner

*Primary Examiner* — Mary Maille Lyons
(74) *Attorney, Agent, or Firm* — Cantor Colburn LLP

(57) ABSTRACT

Provided are a promoter polynucleotide, a signal polypeptide and a polynucleotide encoding the signal polypeptide, and use thereof. A vector and a host cell each including the promoter polynucleotide and the polynucleotide encoding the signal polypeptide may efficiently express and/or extracellularly secrete a foreign protein.

17 Claims, 3 Drawing Sheets

Specification includes a Sequence Listing.

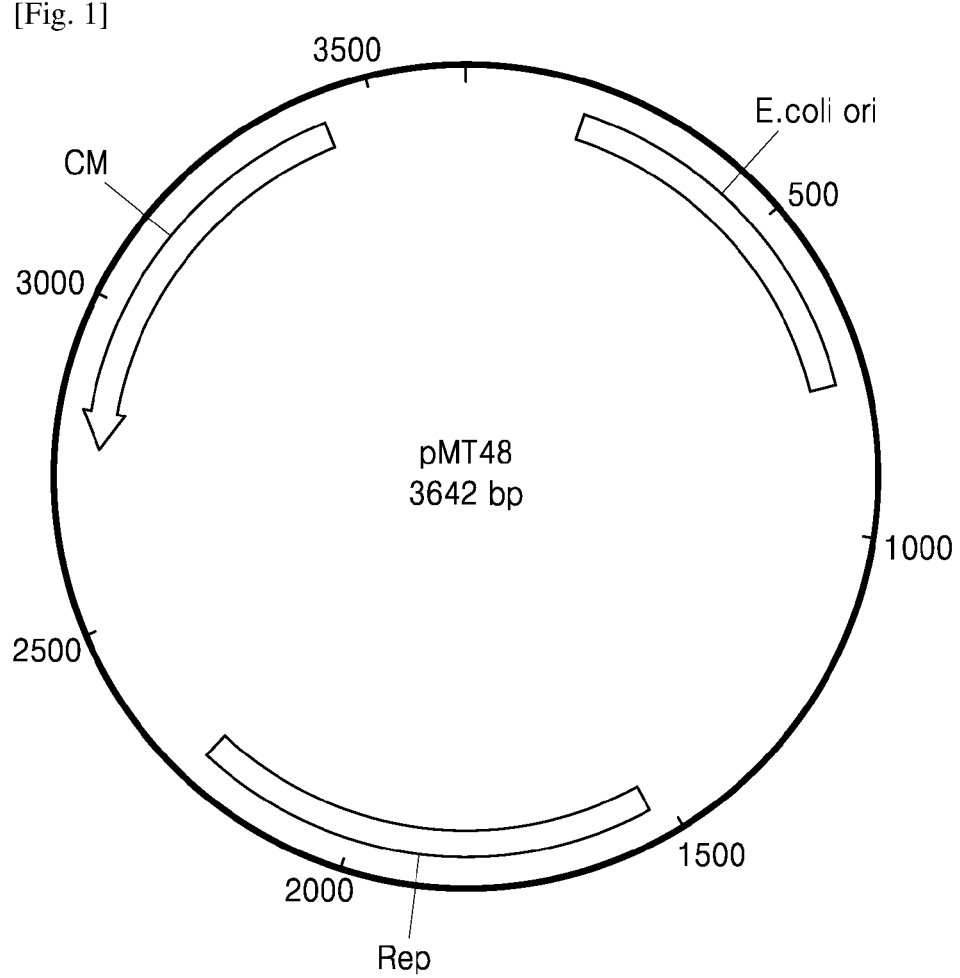
[Fig. 1]

[Fig. 2]
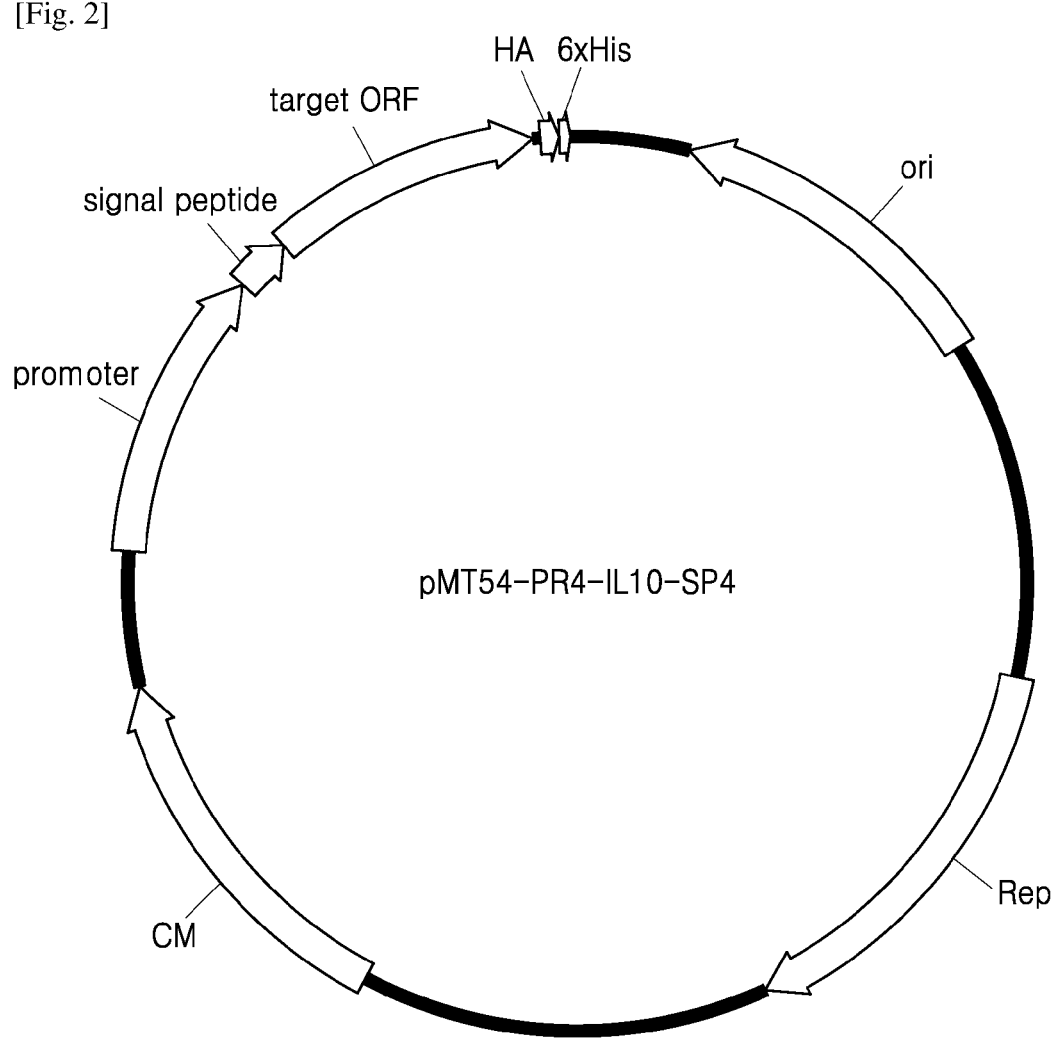
[Fig. 3]
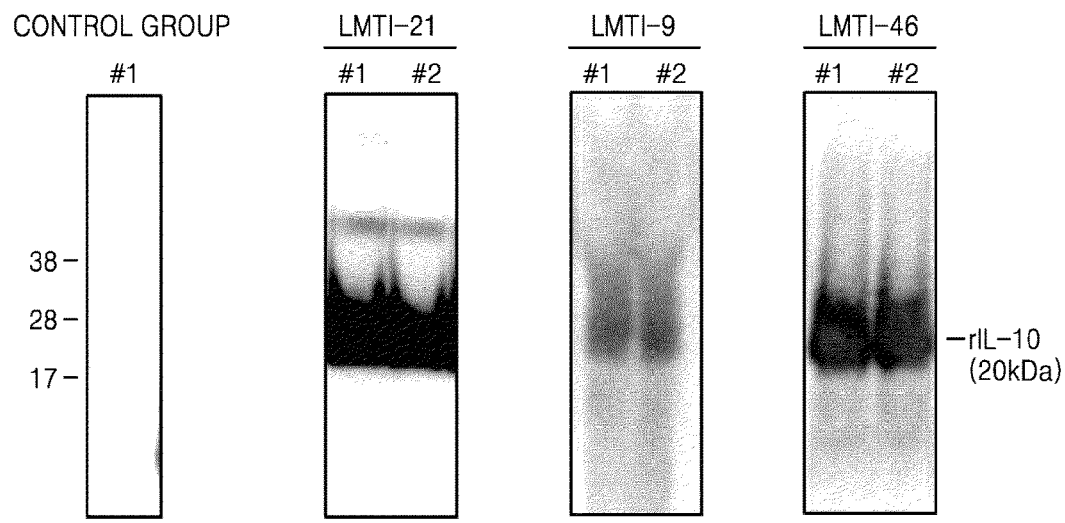

[Fig. 4]
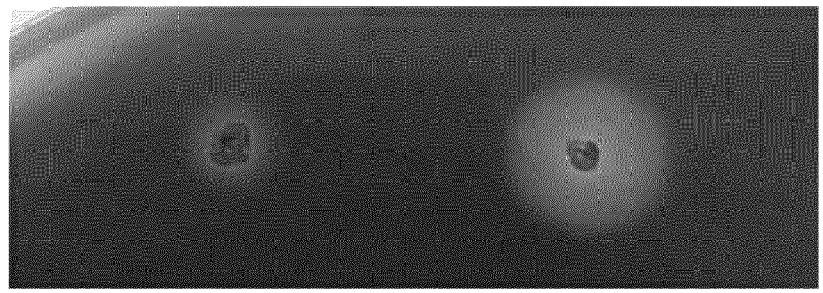
[Fig. 5]
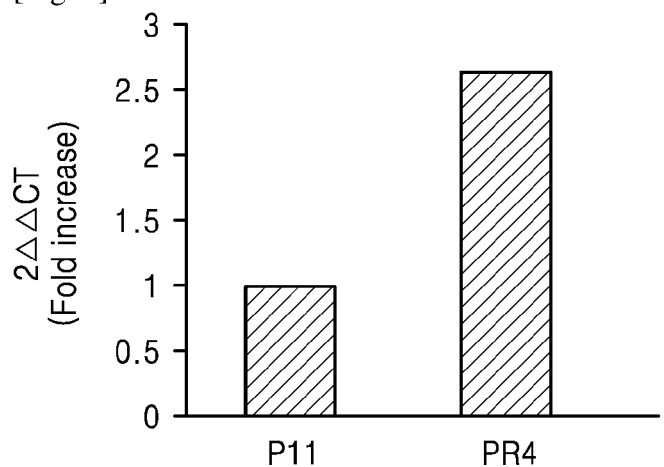
[Fig. 6]
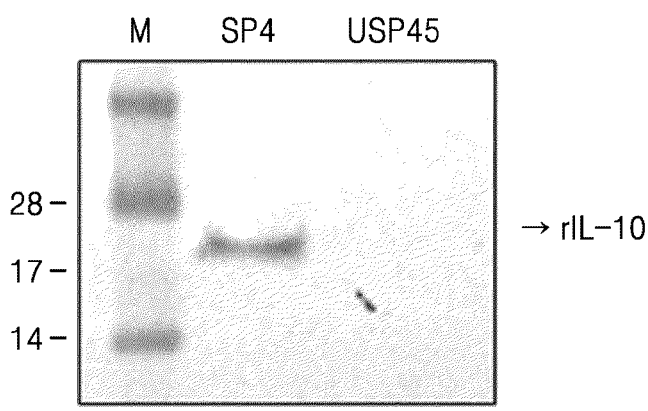

SEQUENCE LISTING

```
<160> NUMBER OF SEQ ID NOS: 23

<210> SEQ ID NO 1
<211> LENGTH: 31
<212> TYPE: DNA
<213> ORGANISM: Lactobacillus paracasei

<400> SEQUENCE: 1
tcgtcacggc gctgcttttt tcatacaaaa t                                31

<210> SEQ ID NO 2
<211> LENGTH: 31
<212> TYPE: PRT
<213> ORGANISM: Lactobacillus paracasei
```

-continued

```
<400> SEQUENCE: 2

Met Lys Phe Asn Lys Val Met Ile Thr Leu Val Ala Ala Val Thr Leu
1               5                   10                  15

Ala Gly Ser Ala Ser Ala Val Thr Pro Val Phe Ala Asp Thr Ser
            20                  25                  30

<210> SEQ ID NO 3
<211> LENGTH: 93
<212> TYPE: DNA
<213> ORGANISM: Lactobacillus paracasei

<400> SEQUENCE: 3
atgaaattca ataaagtcat gatcacgttg gttgctgcag ttaccttagc aggttctgct     60
agcgccgtaa caccagtttt cgctgataca agc                                 93

<210> SEQ ID NO 4
<211> LENGTH: 39
<212> TYPE: DNA
<213> ORGANISM: Artificial Sequence
<220> FEATURE:
<223> OTHER INFORMATION: primer

<400> SEQUENCE: 4
tctgcaggat atccgatcgt ccacaatcaa ggtgcttgg                            39

<210> SEQ ID NO 5
<211> LENGTH: 37
<212> TYPE: DNA
<213> ORGANISM: Artificial Sequence
<220> FEATURE:
<223> OTHER INFORMATION: primer

<400> SEQUENCE: 5
ttactggcag gtcgacgctt gtatcagcga aaactgg                              37

<210> SEQ ID NO 6
<211> LENGTH: 98
<212> TYPE: DNA
<213> ORGANISM: Artificial Sequence
<220> FEATURE:
<223> OTHER INFORMATION: Cloning site

<400> SEQUENCE: 6
aagcttctgc aggatatcgt cgacgcggcc gcagatctca tatggagctc cccgggggat     60
cctctagaac tagtgcatgc cgatcggcta gcctcgag                            98

<210> SEQ ID NO 7
<211> LENGTH: 1723
<212> TYPE: DNA
<213> ORGANISM: Leuconostoc mesenteroides

<400> SEQUENCE: 7
tctgcttttt ggggtttgaa accgtcgttt tttcgacggt ttcttcttat cttgatacta     60
ttagaaacaa cgtcattttc aaaaagtgag gtaaacccett gacacaactg ggtttaggcg   120
tattattgtg gtataaaata aatataaaaa aaacccacgt gagcttcgaa agtttgccga   180
cctcgaacgc gtgagttaat cttgtaaaaa tcgtatttgg atttactaga catagtttaa   240
agcttgaacc ctttgccgtc aagccttctg actgatttaa gtgaagcaag tacataacag   300
attaactctt ctcacgtggt tggtgagggg agttttattt ttggctaatg aaaaagtctt   360
ggttgatcgg tcaaagtcag ggaaagttcg gccgtggcgg gagcgcaagt tggagaactt   420
```

```
gcagtatggt gactatttac aaatattgca ttataagaaa gctcatcgag ttaaagaatg      480
tggcgaagtt ttgcgttttg tggaagataa aaatggtcac aagaaattgg cgcagacttg      540
gttttgccat tctcgtttgt gtccgttatg taattggcgg cgggcaatga agcaatccaa      600
tcagttaaca cagattttga cggaagctgt taaacaacga aagacgggcc ggttcttatt      660
tttaacgttg acggttgaga atacaactgg tgatcaattg aagagtgagt tacgtcaaat      720
gggacgagct gttgcaaaaa ttttcagta tacaaaagtt gccaaaaatt tattgggcta      780
tgtacgttcg actgaagtga ctgttaatca tgaagcgggt cagccaatgt accaccatca      840
tatgcatgtt ttgcttttg tgaagaacca ttattttaag gggactgata actatatttc      900
acaagtagaa tggactggtt tttggcaacg ggcaatgaaa ttgacttatg taccaatggt      960
gaatgttgag gcagttaaac cgaatatgaa tcgccataaa aattcgttat tggctagtgc     1020
tcaagaaacg gctaaatatc aggtaaaatc taaagatatt ttgactaata atcaagaaca     1080
agacctacaa gtaattgatg atttggaacg agctttggct ggttcccggc aaattagcta     1140
tggcggtttg ctgaaagaaa ttcgcaagca gttgcaatta aagacgttg agaatggtga     1200 tttgattaat acggatagtg atgatcaaaa ggttgaccaa gtggtacgcg agattgttgc     1260
taaatgggat tatcaaagaa aaaattattt tacattaaat gagttttgaa atctttaatg     1320
caaaataatt tttaggactt ttaatgtgca ataattttat gacacaatta tttttgttt     1380 tgattctttt aatatttgac tttgtccctg gatacgccat tcatttttt ggggattccc     1440 aagaagggtt tgaattacta gataatataa ttctttct gagttgtata attccacatt     1500
gtctattctt actgctaatg tttctgaata gtcaagttgt tttactttt gttgtcttcc     1560 tgtttcttgc cactttggat ttgcttccat ttttaagatc tactccttt gttttatt     1620 gtgtaactgt gttttattata ctcttgttta gattcaatat ctgacgtttt tgcctcgcag     1680 agctcaaaact ttacgaagta aagtatattg ggctataccct tgc                     1723
```

<210> SEQ ID NO 8
<211> LENGTH: 28
<212> TYPE: DNA
<213> ORGANISM: Artificial Sequence
<220> FEATURE:
<223> OTHER INFORMATION: pLMT1-74rep- For

<400> SEQUENCE: 8

```
aattgaattc tctgctttt ggggtttg                                            28
```

<210> SEQ ID NO 9
<211> LENGTH: 31
<212> TYPE: DNA
<213> ORGANISM: Artificial Sequence
<220> FEATURE:
<223> OTHER INFORMATION: pLMT1-74rep- Rev

<400> SEQUENCE: 9

```
aattgaattc gcaaggtata gcccaatata c                                       31
```

<210> SEQ ID NO 10
<211> LENGTH: 2686
<212> TYPE: DNA
<213> ORGANISM: Artificial Sequence
<220> FEATURE:
<223> OTHER INFORMATION: pUC19 vector

<400> SEQUENCE: 10

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt cgagctcggt acccggggat     420
cctctagagt cgacctgcag gcatgcaagc ttggcgtaat catggtcata gctgtttcct     480
gtgtgaaatt gttatccgct cacaattcca cacaacatac gagccggaag cataaagtgt     540
aaagcctggg gtgcctaatg agtgagctaa ctcacattaa ttgcgttgcg ctcactgccc     600
gctttccagt cgggaaacct gtcgtgccag ctgcattaat gaatcggcca acgcgcgggg     660
agaggcggtt tgcgtattgg cgctcttccg cttcctcgc tcactgactc gctgcgctcg     720
gtcgttcggc tgcggcgagc ggtatcagct cactcaaagg cggtaatacg gttatccaca     780
gaatcagggg ataacgcagg aaagaacatg tgagcaaaag gccagcaaaa ggccaggaac     840
cgtaaaaagg ccgcgttgct ggcgtttttc cataggctcc gcccccctga cgagcatcac     900
aaaaatcgac gctcaagtca gaggtggcga acccgacag gactataaag ataccaggcg     960
tttccccctg gaagctccct cgtgcgctct cctgttccga ccctgccgct taccggatac    1020
ctgtccgcct ttctcccttc gggaagcgtg gcgctttctc atagctcacg ctgtaggtat    1080
ctcagttcgg tgtaggtcgt tcgctccaag ctgggctgtg tgcacgaacc cccgttcag    1140
cccgaccgct gcgccttatc cggtaactat cgtcttgagt ccaacccggt aagacacgac    1200
ttatcgccac tggcagcagc cactggtaac aggattagca gagcgaggta tgtaggcggt    1260
gctacagagt tcttgaagtg gtggcctaac tacggctaca ctagaagaac agtatttggt    1320
atctgcgctc tgctgaagcc agttaccttc ggaaaaagag ttggtagctc ttgatccggc    1380
aaacaaacca ccgctggtag cggtggtttt tttgtttgca agcagcagat tacgcgcaga    1440
aaaaaaggat ctcaagaaga tcctttgatc ttttctacgg ggtctgacgc tcagtggaac    1500
gaaaactcac gttaagggat tttggtcatg agattatcaa aaaggatctt cacctagatc    1560
cttttaaatt aaaaatgaag ttttaaatca atctaaagta tatatgagta aacttggtct    1620
gacagttacc aatgcttaat cagtgaggca cctatctcag cgatctgtct atttcgttca    1680
tccatagttg cctgactccc cgtcgtgtag ataactacga tacgggaggg cttaccatct    1740
ggccccagtg ctgcaatgat accgcgagac ccacgctcac cggctccaga tttatcagca    1800
ataaaccagc cagccggaag ggccgagcgc agaagtggtc ctgcaacttt atccgcctcc    1860
atccagtcta ttaattgttg ccgggaagct agagtaagta gttcgccagt taatagtttg    1920
cgcaacgttg ttgccattgc tacaggcatc gtggtgtcac gctcgtcgtt tggtatggct    1980
tcattcagct ccggttccca acgatcaagg cgagttacat gatcccccat gttgtgcaaa    2040
aaagcggtta gctccttcgg tcctccgatc gttgtcagaa gtaagttggc cgcagtgtta    2100
tcactcatgg ttatggcagc actgcataat tctcttactg tcatgccatc cgtaagatgc    2160
ttttctgtga ctggtgagta ctcaaccaag tcattctgag aatagtgtat gcggcgaccg    2220
agttgctctt gcccggcgtc aatacgggat aataccgcgc cacatagcag aactttaaaa    2280
```

```
gtgctcatca ttggaaaacg ttcttcgggg cgaaaactct caaggatctt accgctgttg    2340
agatccagtt cgatgtaacc cactcgtgca cccaactgat cttcagcatc ttttactttc    2400
accagcgttt ctgggtgagc aaaaacagga aggcaaaatg ccgcaaaaaa gggaataagg    2460
gcgacacgga aatgttgaat actcatactc ttccttttc aatattattg aagcatttat    2520
cagggttatt gtctcatgag cggatacata tttgaatgta tttagaaaaa taaacaaata    2580
ggggttccgc gcacatttcc ccgaaaagtg ccacctgacg tctaagaaac cattattatc    2640
atgacattaa cctataaaaa taggcgtatc acgaggccct ttcgtc                   2686
```

<210> SEQ ID NO 11
<211> LENGTH: 589
<212> TYPE: DNA
<213> ORGANISM: Escherichia coli

<400> SEQUENCE: 11

```
tttccatagg ctccgccccc ctgacgagca tcacaaaaat cgacgctcaa gtcagaggtg     60
gcgaaacccg acaggactat aaagatacca ggcgtttccc cctggaagct ccctcgtgcg    120
ctctcctgtt ccgaccctgc cgcttaccgg atacctgtcc gcctttctcc cttcgggaag    180
cgtggcgctt tctcatagct cacgctgtag gtatctcagt tcggtgtagg tcgttcgctc    240
caagctgggc tgtgtgcacg aaccccccgt tcagcccgac cgctgcgcct tatccggtaa    300
ctatcgtctt gagtccaacc cggtaagaca cgacttatcg ccactggcag cagccactgg    360
taacaggatt agcagagcga ggtatgtagg cggtgctaca gagttcttga agtggtggcc    420
taactacggc tacactagaa gaacagtatt tggtatctgc gctctgctga agccagttac    480
cttcggaaaa agagttggta gctcttgatc cggcaaacaa accaccgctg gtagcggtgg    540
tttttttgtt tgcaagcagc agattacgcg cagaaaaaaa ggatctcaa                589
```

<210> SEQ ID NO 12
<211> LENGTH: 471
<212> TYPE: DNA
<213> ORGANISM: Mus musculus

<400> SEQUENCE: 12

```
caatacagcc gagaggataa ctcttgcact cacttcccgg tgggccagag ccacatgttg     60
ttggaattaa gaacagcttt ctcacaggta aaaactttct tccaaacaaa ggatcagttg    120
gacaatattt tattgacaga ttcattgatg caagacttca aaggctattt gggttgccag    180
gcgcttagcg aaatgataca gttctatctt gtcgaggtga tgccgcaggc agagaagcat    240
ggccctgaga taaaagagca tttgaacagc ttgggagaaa aattgaaaac ccttcgtatg    300
agattacgac gttgtcatag attcttgccg tgccgagaaca agtcaaaggc tgtagagcaa    360
gtcaaaagcg actttaacaa attgcaggac caaggggtat acaaggcaat gaatgaattt    420
gacatcttta tcaactgcat agaggcgtac atgatgatta aaatgaagag t              471
```

<210> SEQ ID NO 13
<211> LENGTH: 18
<212> TYPE: DNA
<213> ORGANISM: Artificial Sequence
<220> FEATURE:
<223> OTHER INFORMATION: primer

<400> SEQUENCE: 13

```
ttttgacctc acccttaa                                                   18
```

```
<210> SEQ ID NO 14
<211> LENGTH: 15
<212> TYPE: DNA
<213> ORGANISM: Artificial Sequence
<220> FEATURE:
<223> OTHER INFORMATION: primer

<400> SEQUENCE: 14
caatacagcc gagag                                                          15

<210> SEQ ID NO 15
<211> LENGTH: 81
<212> TYPE: DNA
<213> ORGANISM: Lactococcus lactis

<400> SEQUENCE: 15
atgaaaaaaa agattatctc agctatttta atgtctacag tgatactttc tgctgcagcc         60
ccgttgtcag gtgtttacgc t                                                   81

<210> SEQ ID NO 16
<211> LENGTH: 30
<212> TYPE: DNA
<213> ORGANISM: Artificial Sequence
<220> FEATURE:
<223> OTHER INFORMATION: primer

<400> SEQUENCE: 16
gatacaagcg tcgaccaata cagccgagag                                          30

<210> SEQ ID NO 17
<211> LENGTH: 30
<212> TYPE: DNA
<213> ORGANISM: Artificial Sequence
<220> FEATURE:
<223> OTHER INFORMATION: primer

<400> SEQUENCE: 17
ggaagcggag gtaccctcga gttatcaatg                                          30

<210> SEQ ID NO 18
<211> LENGTH: 60
<212> TYPE: DNA
<213> ORGANISM: Artificial Sequence
<220> FEATURE:
<223> OTHER INFORMATION: P11 promoter

<400> SEQUENCE: 18
agatctagcg ctatagttgt tgacagaatg gacatactat gatatattgt tgctatagcg         60

<210> SEQ ID NO 19
<211> LENGTH: 2774
<212> TYPE: DNA
<213> ORGANISM: Lactobacillus amylovorus

<400> SEQUENCE: 19
gctagtgata cgacatcaac tgatcactca agcaatgata cagctgattc tgttagcgac         60
ggtgttattt tgcatgcatg gtgctggtcg ttcaacacga ttaaaaacaa cttgaaacag        120
attcatgacg ccggctacac agcggttcaa acttcacctg ttaatgaagt taagttgga         180 aatagcgggt ctaagtcatt aaataactgg tattggctat atcagccaac taaatatagt        240
attggtaact attatttagg aacggaagct gaatttaagt caatgtgcgc tgctgctaaa        300
gaatataata tcaggatcat tgtcgatgca actctgaatg atacaacaag tgattatagt        360
```

```
gcaatttcgg atgaaattaa aagtatttca gattggacac atggtaacac acaaatttcg    420
aattggagtg atcgtgaaga tgttactcaa aattcgttgt taggtttcta tgattggaat    480
actcaaaatt ctcaagttca gacgtatttg aagaatcatt tggaacgctt gatttctgac    540
ggagcttcag gcttccgtta tgatgcagct acgcatattg aacttccaag tcaatatgat    600
ggcagctatg gcagcaattt ctggccaaat attactgata atgggtctga atttcagtat    660
ggtgaagttt tgcaggactc gatttcaaaa gaatcagatt atgctaatta catgagtgtt    720
acagcttcaa attacggcaa tacgattcgc aatgcgttaa agaatcgtga ttttaccgca    780
agtactttgc agaatttcaa catcagtgtt ccagcttcta aattagtaac ttgggtcgaa    840
tcgcatgata attatgctaa cgatgatcaa gtttcgactt ggatgaatag tagtgatatt    900
aaattaggct gggctgttgt tgcttcgcgt tctggtagtg ttccgctgtt ctttgaccgt    960
ccagttgatg gtggtaatgg tactcggttc cctggcagtt cagaaattgg tgatgctggc   1020
agcagtttgt attatgataa agcagttgta gctgttaata aattccataa tgcaatggct   1080
ggtcaatctg aatatatttc taatccaaat ggcaatacca agattttga aaatgaacgt    1140 ggcagcaaag gggttgtttt tgcaaacgct tccgacagtt catatagttt gaatgttaaa   1200
actagtttag ctgatgggac ttatgaaaac aaggctggtt cagatgaatt taccgttaaa   1260
aatggttatt taaccggtac aattcaagga cgtgaagttg ttgttcttta cggggatcca   1320
acaagcagca gcagtacaac aacagaaact aaaaaggttt attttgaaaa gccttcaagt   1380
tggggtagta gagtttatgc ctatgtttat aataaaaata cgaataaagc tataacttca   1440
gcttggcctg gcaaaaaaat gaccgcttta ggtaacgaca aatatgaatt ggatctcgac   1500
actgatgaag atgactctga tttagctgtt atctttaccg atgggacaaa gcaaacacca   1560
gcagctaatg aggctggttt tacctttacg gctgatgcca cttatgatca aatggtgtc    1620 gtaaaaaagg tttattttga aaagccttca agttggggta gtagagttta tgcctatgtt   1680
tataataaaa atacgaataa agctataact tcagcttggc ctggcaaaaa aatgaccgct   1740
ttaggtaacg acaaatatga attggatctc gacactgatg aagatgactc tgatttagct   1800
gttatcttta ccgatgggac aaagcaaaca ccagcagcta atgaggctgg ttttacctt    1860 acggctgatg ccacttatga tcaaaatggt gtcgtaaaaa aggtttattt tgaaaagcct   1920
tcaagtgggg tagtagagt ttatgcctat gtttataata aaaatacgaa taaagctata    1980
acttcagctt ggcctggcaa aaaatgacc gctttaggta acgacaaata tgaattggat    2040
ctcgacactg atgaagatga ctctgattta gctgttatct ttaccgatgg gacaaagcaa   2100
acaccagcag ctaatgaggc tggttttacc tttacggctg atgccactta tgatcaaaat   2160
ggtgtcgtaa aaaaggttta ttttgaaaag ccttcaagtt ggggtagtag agtttatgcc   2220
tatgtttata aaaaatac gaataaagct ataacttcag cttggcctgg caaaaaatg     2280 accgctttag gtaacgacaa atatgaattg gatctcgaca ctgatgaaga tgactctgat   2340
ttagctgtta tctttaccga tgggacaaag caaacaccag cagctaatga ggctggtttt   2400
acctttacgg ctgatgccac ttatgatcaa atggtgtcg taaaaaaggt ttattttgaa    2460
aagccttcaa gttggggtag tagagtttat gcctatgttt ataataaaaa tacgaataaa   2520
gctataactt cagcttggcc tggcaaaaaa atgaccgctt taggtaacga caaatatgaa   2580
ttggatctcg acactgatga agatgactct gatttagctg ttatctttac cgatgggaca   2640
aagcaaacac cagcagctaa tgaggctggt tttacccttta cggctgatgc cacttatgat   2700
```

-continued

```
caaaatggtg tcgtaagaac ttctgattca agcagcacat caagcaattc gtaagccgat    2760
accagcagtt catc                                                      2774

<210> SEQ ID NO 20
<211> LENGTH: 20
<212> TYPE: DNA
<213> ORGANISM: Artificial Sequence
<220> FEATURE:
<223> OTHER INFORMATION: primer

<400> SEQUENCE: 20
aggcgcttag cgaaatgata                                                  20

<210> SEQ ID NO 21
<211> LENGTH: 20
<212> TYPE: DNA
<213> ORGANISM: Artificial Sequence
<220> FEATURE:
<223> OTHER INFORMATION: primer

<400> SEQUENCE: 21
ccttggtcct gcaatttgtt                                                  20

<210> SEQ ID NO 22
<211> LENGTH: 38
<212> TYPE: DNA
<213> ORGANISM: Artificial Sequence
<220> FEATURE:
<223> OTHER INFORMATION: primer

<400> SEQUENCE: 22
tgatacaagc gtcgacgcta gtgatacgac atcaactg                              38

<210> SEQ ID NO 23
<211> LENGTH: 40
<212> TYPE: DNA
<213> ORGANISM: Artificial Sequence
<220> FEATURE:
<223> OTHER INFORMATION: primer

<400> SEQUENCE: 23
cggaggtacc ctcgagttat caatggtgat ggtgatggtg                            40
```

PROMOTER POLYNUCLEOTIDE, SIGNAL POLYPEPTIDE AND USE THEREOF

CROSS-REFERENCE TO RELATED APPLICATION

This application claims the benefit of Korean Patent Application No. 10-2017-0184819, filed on Dec. 29, 2017, in the Korean Intellectual Property Office, the disclosure of which is incorporated herein in its entirety by reference.

TECHNICAL FIELD

Field

The present disclosure relates to a promoter polynucleotide, a signal polypeptide, and use thereof.

Background Art

Microorganisms such as bacteria, yeast, and fungi are becoming increasingly important as hosts for recombinant expression.

Bacteria such as *Lactobacillus* or *Streptococcus* sp. may be useful as delivery vehicles. In addition, generally recognized as safe (GRAS) microorganisms may be administered to humans or animals.

To achieve a high expression level of a foreign product in lactic acid bacteria, there is a demand for novel promoter and signal polypeptides that may be isolated from lactic acid bacteria and may express and secrete the foreign product, in particular a protein, at a high level.

DISCLOSURE OF INVENTION

Technical Problem

An aspect provides an isolated promoter.

Another aspect provides a recombinant polynucleotide including the promoter.

Still another aspect provides a host cell including the recombinant polynucleotide.

Still another aspect provides a method of producing a product using the host cell.

Still another aspect provides an isolated signal polypeptide and a polynucleotide encoding the same.

Still another aspect provides a recombinant polynucleotide including the polynucleotide encoding the isolated signal polypeptide.

Still another aspect provides a host cell including the recombinant polynucleotide encoding the isolated signal polypeptide.

Still another aspect provides a method of producing a protein using the host cell including the recombinant polynucleotide encoding the isolated signal polypeptide.

Solution to Problem

An aspect provides an isolated promoter including a polynucleotide having a sequence identity of 85% or more with a nucleotide sequence of SEQ ID NO: 1 (hereinafter, referred to as 'PR4 promoter').

Another aspect provides a recombinant polynucleotide including the promoter. As used herein, the term "promoter" refers to a nucleic acid molecule, particularly, a region on a DNA molecule, to which an RNA polymerase binds to initiate transcription. The promoter is generally located upstream, i.e., 5' of a sequence to be transcribed, which is regulated by the promoter. The promoter may be a constitutive promoter. The promoter may have a sequence identity of 80% or higher, 85% or higher, 90% or higher, 95% or higher, 96% or higher, 97% or higher, 98% or higher, 99% or higher, or 100% with the nucleotide sequence of SEQ ID NO: 1. The promoter may have the nucleotide sequence of SEQ ID NO: 1.

The recombinant polynucleotide may be a vector. As used herein, the term "vector" refers to a nucleic acid molecule capable of propagate another nucleic acid linked thereto. The vector may include a vector as a self-replicating nucleic acid structure as well as a vector incorporated into the genome of a host cell into which it has been introduced. An expression vector refers to a vector that directs expression of a nucleic acid operably linked thereto. The vector may be a plasmid or a vector derived from a virus.

The vector may be a cloning vector or an expression vector. The expression vector may include a nucleotide sequence encoding a protein, the nucleotide sequence being operably linked to the promoter.

The expression vector may include the promoter, and a first polynucleotide including a nucleotide sequence encoding a product, the first polynucleotide being operably linked to the promoter. The product may include any product which may be produced by expression of the first polynucleotide. The product may be a polypeptide or a nucleic acid. The polypeptide may be a cytokine such as IL-10 or an enzyme such as amylase. The nucleic acid may be DNA or RNA.

As used herein, the term "operably linked" means a linkage that allows transcription or translation to produce a functional transcription or translation product.

The vector may further include one or more selected from the group consisting of a ribosome binding site (RBS), a cloning site, a selection marker gene, a transcription terminator, and a translation initiator factor. The cloning site may be operably linked to the promoter. The cloning site may be a multiple cloning site.

The recombinant polynucleotide may be a recombinant polynucleotide wherein a second polynucleotide encoding a signal polypeptide including an amino acid sequence having a sequence identity of 85% or more with an amino acid sequence of SEQ ID NO: 2 (hereinafter, referred to as "SP4 signal polypeptide") is operably linked between the promoter and the first polynucleotide. In this case, the first polynucleotide may encode a polypeptide.

As used herein, the term "signal polypeptide" refers to a sequence that is present at the N-terminus of a secreted protein precursor but not present in a naturally existing mature protein. The signal polypeptide may be cleaved off from the protein precursor. In general, the signal polypeptide may be cleaved by a protease when extracellularly secreted. The protease may be generally called signal peptidase. The signal polypeptide may have a sequence identity of 80% or more, 85% or more, 90% or more, 95% or more, 96% or more, 97% or more, 98% or more, 99% or more, or 100% with the amino acid sequence of SEQ ID NO: 2. The signal polypeptide has activity to allow extracellular secretion of an expression product of a gene which is fused in frame to the nucleotide sequence encoding the signal polypeptide.

As used herein, the term "secretion" of a protein or a polypeptide molecule may include transport of the protein or the polypeptide molecule outside of a bacterial cell, presence of the protein or the polypeptide molecule in a completely free form in a medium, presence of only part of the protein or the polypeptide molecule outside the bacterial cell, and presence of the protein or the polypeptide molecule on the surface of the bacterial cell.

The signal polypeptide may be derived from *L. paracasei* and may have a secretion-promoting ability. The second polynucleotide may have a nucleotide sequence of SEQ ID NO: 3.

Another aspect provides a host cell including the recombinant polynucleotide. The host cell may be a bacterial cell. The bacterial cell may be a Gram-positive bacterium. The bacterial cell may be a lactic acid bacterium or may belong to the genus *Escherichia*. The lactic acid bacterium may be the genus *Lactobacillus, Lactococcus, Bifidobacteria, Streptococcus, Leuconostoc, Weissella, Pediococcus*, or *Enterococcus*.

The recombinant polynucleotide may be introduced into the host cell by a common nucleic acid introduction method. The nucleic acid introduction method may include electroporation, transformation, transduction, or transfection.

Still another aspect provides a method of producing a product or a metabolite thereof, the method including producing the product by culturing the host cell in a medium; and isolating the product or the metabolite thereof from the culture. The product may include any product that may be produced by expression of the first polynucleotide. The product may be a polypeptide or a nucleic acid. The polypeptide may be a cytokine such as IL-10 or an enzyme such as amylase. The nucleic acid may be DNA or RNA. The metabolite may be a substance produced when the product exerts its activity in a cell. For example, when the product is an enzyme, the metabolite may be a direct product produced when the enzyme exerts its enzymatic activity, or a substance produced from a metabolic pathway in which the enzyme is involved.

In the method, the culturing may be performed by a common method known in the art according to a host cell selected. The medium used in the culturing may include, as a sugar source, for example, carbohydrate e.g., glucose, saccharose, lactose, fructose, maltose, and starch, oil and fat, e.g., soybean oil, sunflower oil, castor oil, coconut oil, etc., a fatty acid, e.g., palmitic acid, stearic acid, and linolenic acid, glycerol, and an organic acid, e.g., acetic acid, singly or in a mixture. The medium may include, as a nitrogen source, for example, peptone, a yeast extract, a meat extract, a malt extract, corn steep liquor, soy meal, urea, or an inorganic compound, e.g., ammonium sulfate, ammonium chloride, ammonium phosphate, ammonium carbonate, or ammonium nitrate, singly or in a mixture. The medium may include, as a phosphorous source, for example, potassium dihydrogen phosphate, dipotassium hydrogen phosphate, or a corresponding sodium-containing salt thereof. The medium may include, for example, a metal salt, e.g., magnesium sulfate or iron sulfate, which is required for growth. Also, in the culturing, substances required for growth, such as amino acids and vitamins, or suitable precursors may be added to the culture. Those components may be added to the culture in a proper manner, for example, in a batch or continuous manner during the culturing.

The culturing may be performed under aerobic conditions, microareobic, unaerobic conditions, or a combination thereof.

The method may further include isolating the product from the culture. The isolating may be performed by an appropriate method according to a kind of a product to be selected. When the product is a protein, the isolating may include isolating the protein from a supernatant after removing cells by centrifugation of the culture, or isolating the protein by cell disruption after recovering the cells. The isolating may be subjected to one or more processes of salting-out, precipitation, chromatography, centrifugation, and filtration. The chromatography may be one or more of anion exchange chromatography, cation exchange chromatography, size exclusion chromatography, and affinity chromatography.

Still another aspect provides an isolated signal polypeptide including an amino acid sequence having sequence identity of 85% or more with the amino acid sequence of SEQ ID NO: 2. The signal polypeptide may have sequence identity of 80% or more, 85% or more, 90% or more, 95% or more, 96% or more, 97% or more, 98% or more, 99% or more, or 100% with the amino acid sequence of SEQ ID NO: 2.

Still another aspect provides a polynucleotide encoding the signal polypeptide. The polynucleotide encoding the signal polypeptide may have a nucleotide of SEQ ID NO: 3.

Still another aspect provides an expression vector including the second polynucleotide encoding the signal polypeptide and the first polynucleotide encoding the protein, wherein the second polynucleotide is operably linked to the promoter and the first polynucleotide is fused in frame to the second polynucleotide.

Still another aspect provides a host cell including the expression vector. The host cell may be a bacterial cell. The bacterial cell may be a Gram-positive bacterium. The bacterial cell may be a lactic acid bacterium or may belong to the genus *Escherichia*. The lactic acid bacterium may be the genus *Lactobacillus, Lactococcus, Bifidobacteria, Streptococcus, Leuconostoc, Weissella, Pediococcus*, or *Enterococcus*.

The recombinant polynucleotide may be introduced into the host cell by a common nucleic acid introduction method. The nucleic acid introduction method may include electroporation, transformation, transduction, or transfection.

Still another aspect provides a method of producing a protein, the method including producing the protein by culturing the host cell in a medium; and isolating the protein from the culture.

In the method, the culturing may be performed by a common method known in the art according to a host cell to be selected. The medium used in the culturing may include, as a sugar source, for example, carbohydrate e.g., glucose, saccharose, lactose, fructose, maltose, and starch, oil and fat, e.g., soybean oil, sunflower oil, castor oil, coconut oil, etc., a fatty acid, e.g., palmitic acid, stearic acid, and linolenic acid, glycerol, and an organic acid, e.g., acetic acid, singly or in a mixture. The medium may include, as a nitrogen source, for example, peptone, a yeast extract, a meat extract, a malt extract, corn steep liquor, soy meal, urea, or an inorganic compound, e.g., ammonium sulfate, ammonium chloride, ammonium phosphate, ammonium carbonate, or ammonium nitrate, singly or in a mixture. The medium may include, as a phosphorous source, for example, potassium dihydrogen phosphate, dipotassium hydrogen phosphate, or a corresponding sodium-containing salt thereof. The medium may include, for example, a metal salt, e.g., magnesium sulfate or iron sulfate, which is required for growth. Also, in the culturing, substances required for growth, such as amino acids and vitamins, or suitable precursors may be added to the culture. Those components may be added to the culture in a proper manner, for example, in a batch or continuous manner during the culturing.

The culturing may be performed under aerobic conditions, micro aerobic conditions, unaerobic conditions, or a combination thereof.

The method may further include isolating the protein from the culture. The isolating may include isolating the protein from a supernatant after removing cells by centrifugation of the culture, or isolating the protein by cell disruption after recovering the cells. The isolating may be subjected to one or more processes of salting-out, precipitation, chromatography, centrifugation, and filtration. The chromatography may be one or more of anion exchange chromatography, cation exchange chromatography, size exclusion chromatography, and affinity chromatography.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description.

Advantageous Effects of Invention

An isolated promoter and a recombinant polynucleotide including the same according to an aspect may be used in efficiently expressing a foreign gene.

A host cell including the recombinant polynucleotide according to another aspect may be used in efficiently expressing a foreign gene.

A method of producing a product using the host cell according to still another aspect may be used to efficiently produce the product.

An isolated signal polypeptide, a polynucleotide encoding the signal polypeptide, and a recombinant polynucleotide including the polynucleotide according to still another aspect may be used in extracellularly secreting a foreign protein.

A host cell including the recombinant polynucleotide including the polynucleotide encoding the isolated signal polypeptide according to still another aspect may efficiently secrete a product of a foreign gene out of the cell.

A method of producing a protein using the host cell according to still another aspect may be used to efficiently produce the protein.

BRIEF DESCRIPTION OF DRAWINGS

These and/or other aspects will become apparent and more readily appreciated from the following description of the embodiments, taken in conjunction with the accompanying drawings in which:

FIG. 1 illustrates the construction of a shuttle vector pMT48 between *E. coli* and lactic acid bacteria;

FIG. 2 illustrates the construction of a pMT54-PR4-IL10-SP4 vector;

FIG. 3 shows results of examining extracellular expression after transformation of three kinds of lactic acid bacteria with the pMT54-PR4-IL10-SP4 vector;

FIG. 4 shows results of examining extracellular expression after transformation of an LMT1-21 strain with a pMT54-PR4-amylase-SP4 vector;

FIG. 5 shows results of measuring IL-10 mRNA levels from pMT54-P11-IL10-SP4 and pMT54-PR4-IL10-SP4 vectors for comparison of promoter strength; and FIG. 6 shows results of measuring quantities of IL-10 secreted from LMT1-21 transformed with pMT54-PR4-IL10-SP4 or pMT54-PR4-IL10-USP45 for comparison of signal peptide strength.

BEST MODE FOR CARRYING OUT THE INVENTION

Hereinafter, the present disclosure will be described in more detail with reference to Examples. However, these Examples are for illustrative purposes only, and the scope of the present disclosure is not intended to be limited by these Examples.

Example 1: Cloning of Promoter and Signal Polypeptide and Examination of Effects Thereof 1. Cloning of Promoter and Signal Polypeptide A promoter and a nucleotide sequence encoding a signal polypeptide were amplified by PCR. In detail, PCR was performed using a genome of *Lactobacillus paracasei* LMT1-21 (Accession No: KCTC 13422BP) as a template and primers to obtain an amplification product of 593 kb. The used primers were PS4_F/R (SEQ ID NOS: 4 and 5).

The amplification product was ligated to pMT54 vector which had been digested with EcoRV and SalI by Infusion cloning (Clontech). Thereafter, the vector was transformed into *E. coli* Top 10 strain (Invitrogen) by a method of Sambrook et al. (Sambrook et al. Molecular cloning: A laboratory Manual, 2nd edition, 1989). Thereafter, the transformed *E. coli* was spread on an LB plate supplemented with 10 μg/ml chloramphenicol to obtain colonies. The pMT54 vector was recovered from the obtained colonies, followed by sequencing analysis. As a result, the vector was confirmed to include a PR4 (SEQ ID NO: 1)-SP4-econding nucleotide sequence (SEQ ID NO: 3). Hereinafter, this vector is referred to as a pMT54-PR4-SP4 vector.

The pMT54 vector was a vector in which a multiple cloning site (SEQ ID NO: 6) was introduced into HindIII and XhoI restriction sites of pMT48 vector. The multiple cloning site has multiple restriction enzyme recognition sites and is tagged with human influenza hemagglutinin (HA) to confirm expression of a target protein. The pMT48 vector was a vector in which Rep gene (SEQ ID NO: 7) which is an origin of replication of a plasmid pLMT1-74 was introduced into the EcoRI site of pUC19 (New England Biolabs). The pMT48 vector was constructed as follows.

First, a tentative plasmid pLMT1-74 was isolated from a LMT1-74 strain (*Leuconostoc mesenteroides* KCTC 13164BP) which had been isolated from kimchi using a plasmid midi kit (Qiagen, Inc., Valencia, Calif.). PCR was performed using the plasmid pLMT1-74 as a template and oligonucleotides of SEQ ID NOS: 8 and 9 as primers to amplify Rep gene (SEQ ID NO: 7) which is an origin of replication of plasmid pLMT1-74. The amplified product was digested with EcoRI, and ligated to pUC19 which had been digested with the same enzyme to obtain the pMT48 vector. The polynucleotide of SEQ ID NO: 7 may be also chemically synthesized. The vector pUC19 has a nucleotide sequence of SEQ ID NO: 10.

FIG. 1 illustrates the composition of a shuttle vector pMT48 between *E. coli* and lactic acid bacteria. In this vector, Rep has the nucleotide sequence of SEQ ID NO: 7 and is a partial sequence of Rep origin which is an origin of replication of a universal lactic acid bacterial host-vector pLMT1-74, and provides a replication ability for lactic acid bacteria. *E. coli* ori represents an origin of DNA replication of *E. coli*, and has pUC19 ori, i.e., a nucleotide sequence of SEQ ID NO: 11. CM represents a chloramphenicol resistance gene encoding chloramphenicol acetyltransferase.

2. Cloning of Target Protein IL-10

(1) Construction of Experimental Vector: pMT54-PR4-IL10-SP4 Vector

Synthesis of IL-10 gene (SEQ ID NO: 12) was conducted by Macrogen Inc. (Korea). The synthesized gene fragment and the pMT54-PR4-SP4 vector were treated with restriction enzymes SalI and XhoI to cleave cloning sites of the vector. The cleaved product was purified using a Gel purification kit (Bioneer), and dephosphorylated using alkaline phosphatase. To a mixture of 1 μl of the prepared vector DNA, 3 μl of the gene (IL-10), 0.5 μl of T4 DNA ligase (Takara), and 1 μl of buffer, 5.5 μl of distilled water was added to prepare total 10 μl of a reaction mix. This reaction mix was incubated at 16° C. for 12 hours to ligate the gene into the cloning site of the vector. The obtained ligation product was transformed into *E. coli* Top 10 strain in the same manner as above, followed by sequencing. As a result, introduction of the gene was confirmed, and this product was designated as a pMT54-PR4-IL10-SP4 vector. FIG. 2 illustrates the composition of the pMT54-PR4-IL10-SP4 vector. In FIG. 2, promoter, signal peptide, and target gene represent PR4, SP4, and IL-10, respectively. The vector, which is a shuttle vector between *E. coli* and lactic acid bacteria, includes an origin of replication of *E. coli* (origin), an origin of replication of lactic acid bacteria (rep gene), and a chloramphenicol resistance gene. The promoter, signal peptide, target gene, HA tag, and His are linked at the multiple cloning site.

(2) Construction of Control Vector 1: pMT54-PR4-IL10-USP45 Vector

A vector was constructed in the same manner as in the experimental vector, except that the polynucleotide SP4 encoding the signal polypeptide was replaced by USP45 polynucleotide. This is to examine an effect of a different signal polypeptide on extracellular secretion of IL-10 protein when the same promoter was used.

In detail, PCR was performed using the pMT54-PR4-IL10-SP4 vector as a template and oligonucleotides of SEQ ID NOS: 13 and 14 as primers to amplify the vector from which SP4 was excluded. A USP45-encoding polynucleotide (SEQ ID NO: 15) was synthesized (Macrogen, Korea). The amplified product and the USP45-encoding polynucleotide were ligated by an infusion cloning method, and introduced into *E. coli* to clone a pMT54-PR4-IL10-USP45 vector. USP45 is a signal polypeptide derived from *Lactococcus lactis* and is known to play a role in secreting protein products such as homologous proteinase (PrtP) and *Bacillus stearothermophilus*-derived alpha-amylase (van Asseldonk M1, et al. Mol Gen Genet. 1993 September; 240(3):428-34).

(3) Construction of Control Vector 2: pMT54-P11-IL10-SP4 Vector

A vector was constructed in the same manner as in the experimental vector, except that the promoter PR4 was replaced by P11 promoter. This is to examine an effect of a different promoter on expression of IL-10 protein when the same signal polypeptide was used. P11 is a synthetic promoter having a strong transcription initiation activity in *Lactobacillus plantarum* (Lars Axelsson, Microbiology (2006), 152, 1011-019).

In detail, PCR was performed using the pMT54-PR4-IL10-SP4 vector as a template and oligonucleotides of SEQ ID NOS: 16 and 17 as primers to amplify the vector from which PR4 was excluded. P11 promoter (SEQ ID NO: 18) was synthesized (Macrogen, Korea). The amplified product and the P11 promoter were ligated by an infusion cloning method, and introduced into *E. coli* to clone a pMT54-P11-IL10-SP4 vector.

3. Transformation and Expression of IL-10 Protein (1) Expression of IL-10 Protein by pMT54-PR4-IL10-SP4 Vector The pMT54-PR4-IL10-SP4 vector and the pMT54-P11-IL10-SP4 vector were transformed into three different kinds of lactic acid bacteria, respectively. The three different kinds of lactic acid bacteria were *Lactobacillus paracasei* KCTC 13422BP, *Lactobacillus plantarum* KCTC 13421BP, and *Lactobacillus brevis* KCTC 13423BP, all separated from kimchi. These strains are also called LMT1-21, LMT1-9, and LMT1-46, respectively.

Each of the strains was cultured in 50 mL of MRS medium (Difco Co., USA) until $OD_{600}$ reached 0.5, and then centrifuged at 4° C. and 7,000 rpm for 10 minutes. Cell pellets were washed twice with 25 mL of ice-cold EPS (EPS: 1 mM $K_2HPO_4$, 1 mM $KH_2PO_4$, pH 7.4, 1 m MgCl2, and 0.5 M sucrose).

After washing, cells were re-suspended in 1 mL of ice-cold EPS, and competent cells to be used in electroporation were prepared, and stored in a deep freezer at −80° C. 40 μl of competent cells and each 1 μl of vector DNA (1 μg/μl) were put in a cuvette and left on ice for 5 minutes. Electric field pulse was applied thereto under conditions of 25 μF, 8 kV/cm, 400 ohms, and the cells were immediately added to 1 mL of MRS liquid medium, followed by incubation at 37° C. for 1 hour. Thereafter, the incubated cells were spread on MRS medium containing 10 μg/ml of chloramphenicol, followed by incubation at 37° C. for 48 hours.

FIG. 3 shows results of examining extracellular expression after transformation of the three kinds of lactic acid bacteria with the pMT54-PR4-IL10-SP4 vector. In FIG. 3, as a vector of a control group, pMT54-P11-IL10-USP45 was used instead of pMT54-PR4-IL10-SP4.

As shown in FIG. 3, the pMT54-PR4-IL10-SP4 vector showed extracellular expression of IL-10 protein in the three lactic acid bacteria, but the control group showed no expression. These results indicate that the PR4 promoter operated to express the gene and the SP4 signal peptide exerted extracellular secretion of the expressed protein.

(2) Expression at mRNA Level: Examination of Promoter Strength

Each of the pMT54-PR4-IL10-SP4 vector and the pMT54-P11-IL10-SP4 vector was transformed into *Lactobacillus paracasei* KCTC 13422BP (LMT1-21) lactic acid bacterium in the same manner as in (1).

The strain introduced with each of the vector was subjected to stationary culture in MRS medium at 37° C. for 16 hours. 1 ml of the culture was centrifuged at 7,000 rpm for 5 minutes, and then a supernatant was discarded, and a cell pellet was obtained. mRNA was extracted therefrom using an RNA prep kit (Macherey-nagel, cat. no 740955.50) in accordance with the manufacturer's protocol. 100 ng of mRNA was used as a template to synthesize cDNA. cDNA synthesis was performed using a Roketscript cycle RT premix of Bioneer. The synthesized cDNA was used as a template and oligonucleotides of SEQ ID NO: 20 and SEQ ID NO: 21 were used as primers to perform real-time (RT) PCR. RT-PCR was performed using a SYBR premix (takara, RR820B) in accordance with the manufacturer's protocol.

FIG. 5 shows result of RT-PCR which was performed by using cDNA derived from transformed cells as a template. As shown in FIG. 5, as compared with the *L. paracasei* KCTC13422BP transformed with the pMT54-P11-IL10-SP4 vector, i.e., the control vector, the strain transformed with the pMT54-PR4-IL10-SP4 vector showed remarkably high IL-10 mRNA level. These results indicate that the PR4 promoter strongly operates transcription, as compared with the P11 promoter. In FIG. 5, "2ΔΔCT" on Y axis represents an increase of the transcription level relative to that of the control group in the results of analyzing relative transcription levels.

(3) Expression at Protein Level: Examination of Signal Peptide Strength

Each of the pMT54-PR4-IL10-SP4 vector and the pMT54-PR4-IL10-USP45 vector was transformed into *Lactobacillus paracasei* KCTC 13422BP (LMT1-21) lactic acid bacterium in the same manner as in (1).

The strain introduced with each of the vector was subjected to stationary culture in MRS medium at 37° C. for 16 hours. The culture was seeded in MRS liquid medium at 3 (v/v) %, and then subjected to stationary culture at the same temperature for 8 hours. 1 ml of the culture was centrifuged at 7,000 rpm for 5 minutes, and a supernatant was obtained. 100 μl of trichloroacetic acid was added to 1 ml of the supernatant, which was left at 4° C. for 1 hour to concentrate components of the culture. The resultant was centrifuged at 4° C. and 13,000 rpm for 10 minutes, and a pellet was washed with 1 ml of cold acetone once, dried at room temperature for 10 minutes, and eluted with 100 μl of Tris-HCl buffer (pH 8.8).

A 4× loading buffer (Thermo) and a 10× reducing agent (Thermo) were added to the eluate, followed by electrophoresis on SDS-PAGE gel. This gel was transferred onto a nitrocellulose membrane using a Trans blot semi-dry cell (bio-rad), followed by Western blotting. In detail, the membrane was blocked with a TBST buffer containing 1% skim milk for 1 hour, and reacted with anti-HA antibody (santa cruz) at room temperature for 2 hours. The membrane was washed with TBST for 5 minutes three times, and detected using an ECL. In the pMT54-PR4-IL10-SP4 vector, HA gene was operably linked to IL-10 gene at the 3'-terminus thereof, and thus the HA-tagged gene was expressed.

FIG. 6 shows comparison of signal peptide strength by examining quantity of IL-10 secreted from LMT1-21 which was transformed with each of pMT54-PR4-IL10-SP4 and pMT54-PR4-IL10-USP45. As shown in FIG. 6, a larger amount of the expressed protein was secreted by SP4 signal peptide than USP45 signal peptide.

Example 2: Expression of Amylase Gene Using PR4 Promoter and SP4 Sequence

A pMT54-PR4-amylase-SP4 vector was constructed in the same manner as in 2 and 3 of Example 1, except that alpha-amylase gene (SEQ ID NO: 19) instead of IL-10 gene and primers F/R(SEQ ID NOS: 22 and 23) were used, and this vector was transformed into a lactic acid bacterium *L. paracasei* LMT1-21 to examine extracellular expression of alpha-amylase. Amplification of the alpha-amylase gene was performed using genomic DNA of *Lactobacillus* amylovorus (KCTC3597).

Amylase activity of the transformed LMT1-21 strain was examined by an iodine test. First, the LMT1-21 strain introduced with the pMT54-PR4-amylase-SP4 vector was subjected to stationary culture in MRS liquid medium at 37° C. for 12 hours. Thereafter, the culture was applied in small dots to an MRS plate containing 0.5% soluble starch and 10 mg/l of chloramphenicol, and subjected to stationary culture at 37° C. for 12 hours to allow amylase to sufficiently degrade starch. Thereafter, a Lugol's iodine solution (iodine/potassium iodide solution) was evenly applied onto the MRS plate to allow reaction with undegraded starch. As the amylase activity is lower, the amount of remaining starch is larger, and as a result, a strong iodine-starch reaction occurs to show a purple color. On the contrary, as the amylase activity is higher, the amount of starch remaining around cells is smaller, and as a result, a transparent circle is formed.

FIG. 4 shows results of examining extracellular expression after transformation of an LMT1-21 strain with pMT54-PR4-amylase-SP4 vector. In FIG. 4, a vector of a control group is the same as the pMT54-PR4-amylase-SP4 vector, except that P11 promoter was used instead of PR4, and USP45 was used instead of SP4.

As shown in FIG. 4, the experimental group using the pMT54-PR4-amylase-SP4 vector showed formation of a large transparent circle due to extracellular expression of alpha-amylase in LMT1-21 strain whereas the control group showed formation of a small transparent circle due to no expression of alpha-amylase. These results indicate that PR4 operated to express amylase gene and extracellular secretion was increased by SP4.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the disclosure as defined by the following claims.

The invention claimed is:

1. A recombinant polynucleotide comprising a promoter having the nucleotide sequence of SEQ ID NO:1 and further comprising a first polynucleotide operably linked to the promoter, the first polynucleotide encoding a protein and the protein is a foreign protein with regard to *Lactobacillus paracasei*.

2. The recombinant polynucleotide of claim 1, wherein the recombinant polynucleotide is a vector.

3. The recombinant polynucleotide of claim 2, wherein the vector is a cloning vector or an expression vector.

4. The recombinant polynucleotide of claim 3, wherein the vector is the expression vector.

5. The recombinant polynucleotide of claim 1, further comprising a second polynucleotide encoding a signal polypeptide.

6. The recombinant polynucleotide of claim 5, wherein the second polynucleotide encoding a signal polypeptide is operably linked between the promoter and the first polynucleotide.

7. The recombinant polynucleotide of claim 5, wherein the second polynucleotide encoding a signal polypeptide is operably linked to the promoter and the first polynucleotide is fused in frame to the second polynucleotide encoding a signal polypeptide.

8. The recombinant polynucleotide of claim 5, wherein the second polynucleotide encoding a signal polypeptide has the nucleotide sequence of SEQ ID NO:3.

9. A host cell comprising the recombinant polynucleotide of claim 1.

10. The host cell of claim 9, wherein the host cell is a lactic acid bacterium or belongs to the genus *Escherichia*.

11. The host cell of claim 10, wherein the host cell is the lactic acid bacterium.

12. The host cell of claim 11, wherein the lactic acid bacterium belongs to the genus *Lactobacillus, Lactococcus, Bifidobacteria, Streptococcus, Leuconostoc, Weissella, Pediococcus,* or *Enterococcus*.

13. The host cell of claim 9, wherein the recombinant polynucleotide comprises a second polynucleotide encoding a signal polypeptide.

14. A method of producing a protein, the method comprising culturing the host cell of claim 9 in a medium; and recovering the protein from the cell or the medium.

15. The method of claim 14, wherein the protein is recovered from the medium.

16. A method of producing a recombinant cell comprising introducing a vector to a host cell, wherein the host cell is *Lactobacillus paracasei* KCTC 13422BP, *Lactobacillus plantarum* KCTC 13421BP, or *Lactobacillus brevis* KCTC 13423BP, and wherein the vector comprises the recombinant polynucleotide of claim 1.

17. A recombinant polynucleotide comprising a promoter having the nucleotide sequence of SEQ ID NO:1, wherein the recombinant polynucleotide is a vector, wherein the vector comprises *E. coli* ori, which is an origin of DNA replication of *E. coli*.

\* \* \* \* \*